United States Patent [19]

Johnson

[11] Patent Number: 5,089,183
[45] Date of Patent: Feb. 18, 1992

[54] METHOD OF MANUFACTURING APPLIANCES FOR USE IN FILLING ENDODONTICALLY PREPARED ROOT CANALS

[76] Inventor: William B. Johnson, 5010 E. 68th St., Suite 104, Tulsa, Okla. 74136

[21] Appl. No.: 640,045

[22] Filed: Jan. 9, 1991

[51] Int. Cl.$^5$ .............................................. A61C 13/00
[52] U.S. Cl. ...................................... 264/16; 264/219; 264/259
[58] Field of Search ................. 264/16, 259, 271.1, 264/275, 279; 433/87, 226, 228.1, 224; 425/126.2; 249/83

[56] References Cited

U.S. PATENT DOCUMENTS 3,516,753  6/1970  Dickey ............................ 264/275
4,894,011  1/1990  Johnson .......................... 433/81

Primary Examiner—Jan H. Silbaugh
Assistant Examiner—Christopher A. Fiorilla
Attorney, Agent, or Firm—Head and Johnson

[57] ABSTRACT

A method of manufacturing appliances for use in filling endodontically prepared root canals including the steps of forming a mold having a plurality of spaced apart elongated cavities therein, filling each of the cavities with uncured endodontic filler material, inserting into each cavity the shaft portion of a filler carrier, each filler carrier having a handle portion that remains exterior of the mold, placing the mold with the uncured filler material and filler carrier therein in an oven, heating the mold with the uncured filler material and filler carriers therein to cause the filler material to cure and adhere to the filler carrier shaft portions, and removing the filler carriers having the filler material cured thereon, each of which is ready for use as an appliance to fill an endodontically prepared root canal.

5 Claims, 3 Drawing Sheets

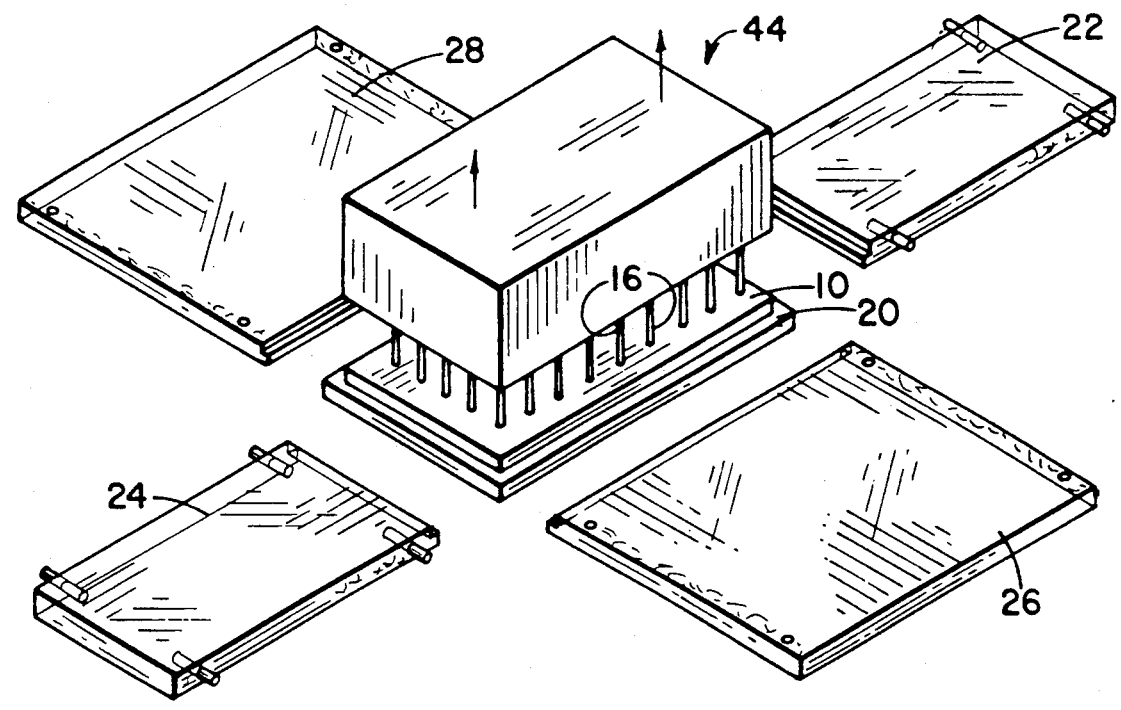
Fig. 8
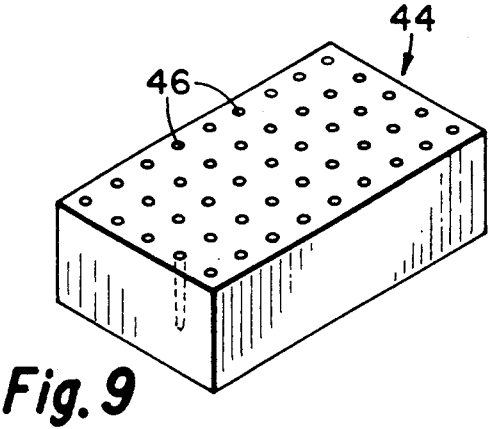
Fig. 9
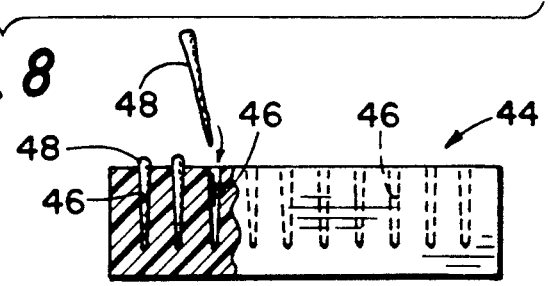
Fig. 10
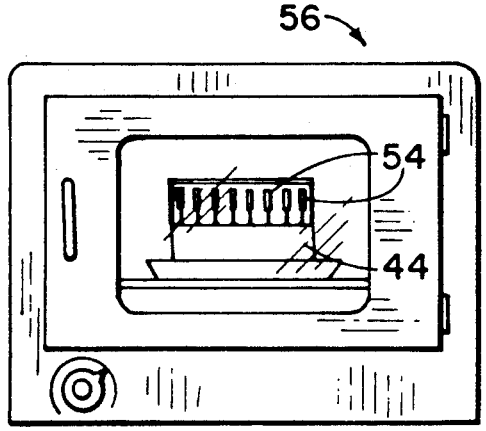
Fig. 12
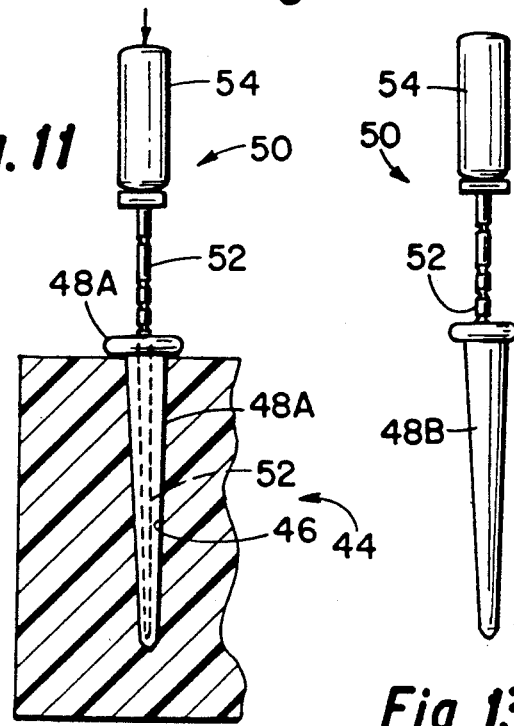
Fig. 11
Fig. 13

METHOD OF MANUFACTURING APPLIANCES FOR USE IN FILLING ENDODONTICALLY PREPARED ROOT CANALS

BACKGROUND OF THE INVENTION

This invention is related to a method of manufacturing appliances for use in filling endodontically prepared root canals of the type described in U.S. Pat. No. 4,758,156, entitled "Tool For Use In Applying Filler Material To An Endodontically Prepared Root Canal" issued July 19, 1988, and U.S. Pat. No. 4,894,011 entitled "Appliance For Use In Applying Filler Material To An Endodontically Prepared Root Canal" issued Jan. 16, 1990, both by William B. Johnson, which patents are incorporated herein by reference. These patents to Dr. Johnson disclose an improved and more expeditious means of filling an endodontically prepared root canal utilizing a filler carrier having cured filler material thereon. The use of prepared appliances of the type shown in U.S. Pat. Nos. 4,758,156 and 4,894,011 has become a standard technique utilized by endodontists in the United States and in many other countries of the world.

This disclosure is specifically directed toward an improved and more expeditious means of manufacturing appliances of the type shown in U.S. Pat. Nos. 4,758,156 and 4,894,011.

SUMMARY OF THE INVENTION

A method of manufacturing appliances for filling endodontically prepared root canals includes the first step (a) of forming a mold having a plurality of spaced apart, elongated cavities of selected shape and length. The diameters and lengths of the cavities may all be the same or of a variety of sizes in one mold. The nominal diameter and length is that of the exterior diameter and length of an appliance having filler material thereon, that is, the diameter and length of the filler covered appliance as it will be inserted into a prepared root canal by an endodontist or dentist.

Step (b) includes filling each of the cavities in the mold with uncured endodontic filler material, such as uncured gutta-percha. This filling step can be accomplished such as by preforming tips of uncured gutta-percha into elongated tapered portions that are then inserted into the cavities. It is not important that the preformed elongated tips of gutta-percha closely fit the interior of the cavities since in the process of heating, as will be described, the material will flow to conform to the cavities. Further, it is not important that the cavities be entirely filled for reasons to be described.

Step (c) includes inserting into each of the cavities the shaft portion of a filler carrier, the filler carrier having a handle portion that remains exterior of the mold. Filler carriers can be of various configurations, examples of which are shown in U.S. Pat. No. 4,758,156. Typically each such carrier includes an elongated shaft, such as of metal or plastic, the shaft forming the distal portion of the filler carrier, and the proximal portion of the filler carrier being an enlarged external diameter handle portion. The handle portion may be configured to be manually manipulated or may be configured to fit into the chuck portion of a mechanical device.

Step (d) consists of placing the mold having the uncured filler material and filler carriers therein in an oven.

Step (e) includes heating the mold with the uncured filler material and filler carriers therein at a selected temperature and for a selected time to cure the filler material and to cause the filler material to adhere to the filler carrier shaft portions. The time and temperature will be determined entirely by the characteristics of the specific filler material employed. The time and temperature can vary and normally the higher the temperature, the shorter the time required for curing the filler material. The maximum temperature must be below that which causes degradation of the filler material. Experimentation is required to establish the best temperature and time required to cure the filler material selected.

In step (f) the mold with the filler carriers having the filler material cured thereon is allowed to slowly cool. This can be accomplished by turning off the oven to let the latent heat of the oven extend the cooling period. Thereafter the filler carriers are each extracted from the individual cavities in the mold. The filler carriers are removed from the mold by grasping the handle portions. The cured filler material adheres to the shaft portions of the filler carriers and the appliances are thereby ready for employment to fill endodontically prepared root canals.

This disclosure also includes a method of making the mold for use in manufacturing endodontic appliances. This method includes the following steps:

(a) Drilling into a base member of solid flat material, such as plastic or metal, a plurality of spaced apart holes;

(b) Inserting into each of the holes in the base member an elongated metal pattern, each of the patterns having the desired configuration of a filler covered carrier portion of an appliance for use in filling an endodontically prepared root canal;

(c) Forming a vessel with the base member as the bottom thereof and with the patterns extending upwardly therein. This can be accomplished by attaching side and end panels extending upwardly from the periphery of the base;

(d) Pouring liquid plastic and catalyst into the vessel to fill the vessel to a depth to a least fully cover the patterns that extend upwardly from the base;

(e) Allowing the plastic having catalyst mixed therewith to solidify; and (f) Removing the mold from the vessel and from the base, the mold having a cavity therein for each of the patterns. Each cavity is then useful for forming an appliance.

A better understanding of the invention will be had by reference to the following description and claims, taken in conjunction with the attached drawings.

DESCRIPTION OF THE DRAWINGS

FIG. 2 shows a plurality of metal patterns extending upwardly from the vessel bottom member.

This illustration is diagrammatic since the plastic and catalyst must be intimately mixed.

Figure 5:
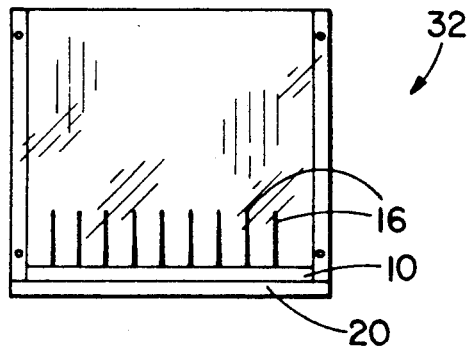
Figure 5:
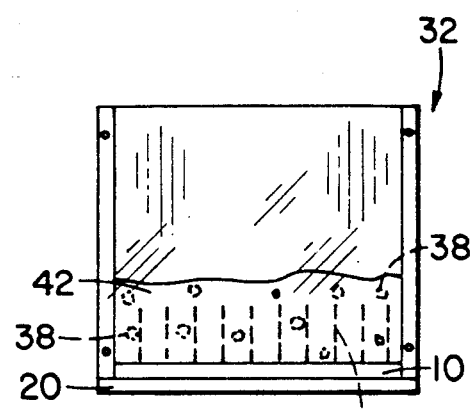

FIG. 5 is an elevational view of the vessel showing the bottom portion of the front panel broken away to illustrate that air bubbles are sometimes inherent in the liquid plastic as it solidifies, which would be deleterious to the functioning of the mold.

Figure 6:
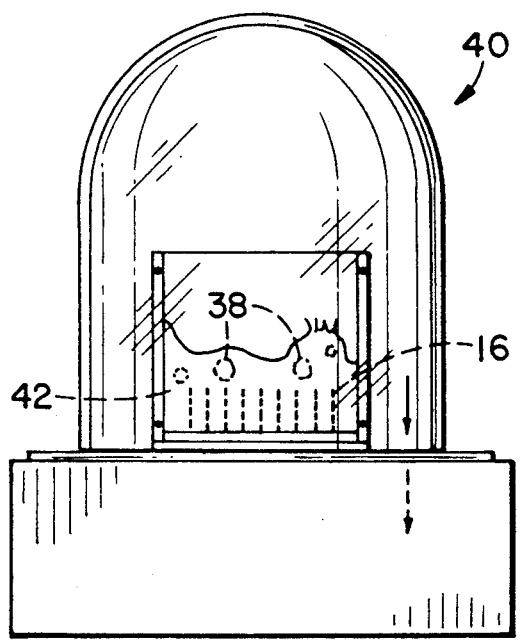

FIG. 6 shows placement of the vessel having the combined liquid plastic and catalyst therein in a vacuum chamber. Vacuum is formed in the chamber to draw out of the liquid plastic any bubbles that have formed therein.

Figure 7:
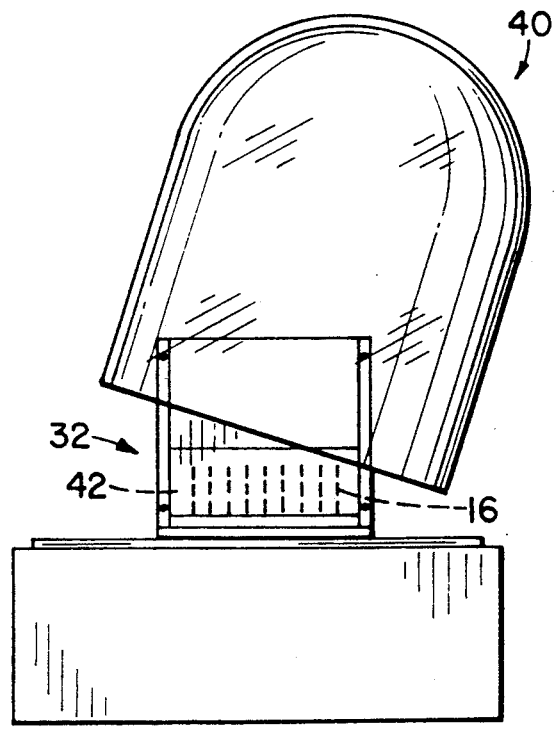

FIG. 7 shows diagrammatically the vacuum chamber being opened to remove the vessel.

FIG. 8 is an exploded view showing the side panels of the vessel being disassembled and with the formed plastic mold being removed from the bottom of the vessel. The mold is ready for use in the manufacture of endodontic appliances.

FIG. 9 is an isometric view of a mold that can be used for manufacture of appliances for filling endodontically prepared root canals. The mold has a generally flat upper surface having a plurality of spaced apart downwardly extending cavities therein. Each cavity is of a selected shape and length according to the ultimately desired appliance.

FIG. 10 shows the mold in elevational view and partially broken away to disclose a cross-sectional portion thereof, the mold being shown in reduced scale. This figure shows the process of filling each of the cavities in the mold with a filler material tip, formed such as of gutta-percha.

FIG. 11 shows the insertion of the distal shaft portion of a filler carrier into one of the plurality of cavities in the mold. A filler carrier is inserted into each of the cavities in the mold.

FIG. 12 shows the mold with each of the cavities therein filled by filler material and having a filler carrier therein. The mold is placed in an oven for the purpose of heating and thereby curing the filler material in each of the mold cavities.

FIG. 13 shows an appliance after it has been removed from the mold following the curing process. The curing process causes the filler material to adhere in a plastic manner to the shaft portion of each filler carrier.

DESCRIPTION OF THE PREFERRED EMBODIMENT

Figure 1:
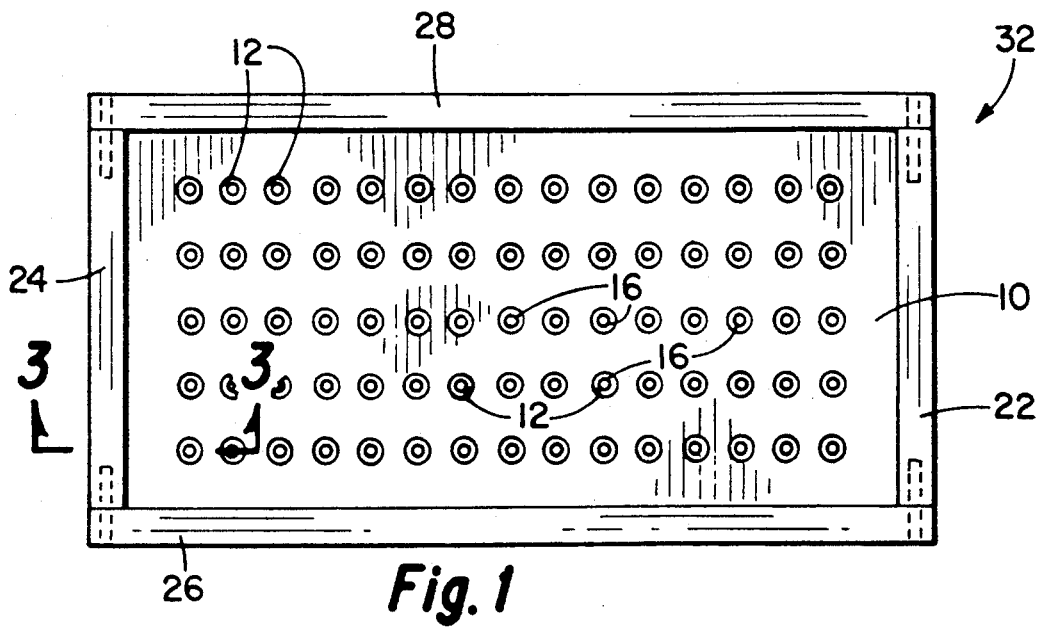
FIG. 1 is a top plan view of a vessel assembled for use in preparing a mold.

Referring to the drawings and first to FIGS. 1-7, the method of manufacturing a mold that is useful in the process of manufacturing appliances for use in filling endodontically prepared root canals is illustrated. The mold is formed utilizing a base 10 of solid material, such as a sheet of plastic. A plurality of holes 12 are drilled in base 10. Positioned within each of the holes 12 is an elongated metal pattern 14. Each of the patterns 14 includes an integral elongated shaft portion 16 and a cylindrical base portion 18, the base portion 18 of each pattern being configured to be received in a hole 12 in the mold base 10. FIG. 1 is a plan view that shows the base 10 with a plurality of patterns 14 with the tapered portions 16 extending uprightly therein. The shaft portion 16 of each pattern 14 may be slightly tapered as shown or may be cylindrical and may be circular in cross-section taken perpendicular to the length of the pattern or of other cross-sectional shapes.

After the base 10 is prepared with the upstanding patterns 14, each having an exposed upstanding shaft portion 16, the base is utilized for forming a vessel. A vessel can be constructed by first positioning base 10 on a flat bottom member 20 (see FIG. 3), the bottom member being preferably of dimensions slightly greater than that of base 10. In the illustrated arrangement base 10 is rectangular which is a preferred arrangement, although, obviously it could be round or any other shape.

To complete the construction of a vessel, vertical end panels 22 and 24, and vertical side panels 26 and 28 are attached to each other and to the bottom portion 20. The side and end panels may be attached by removable screws or pins. To make the vessel leak-proof, wax 30 may be applied between the edges of the end panels and side panels.

Figure 2:
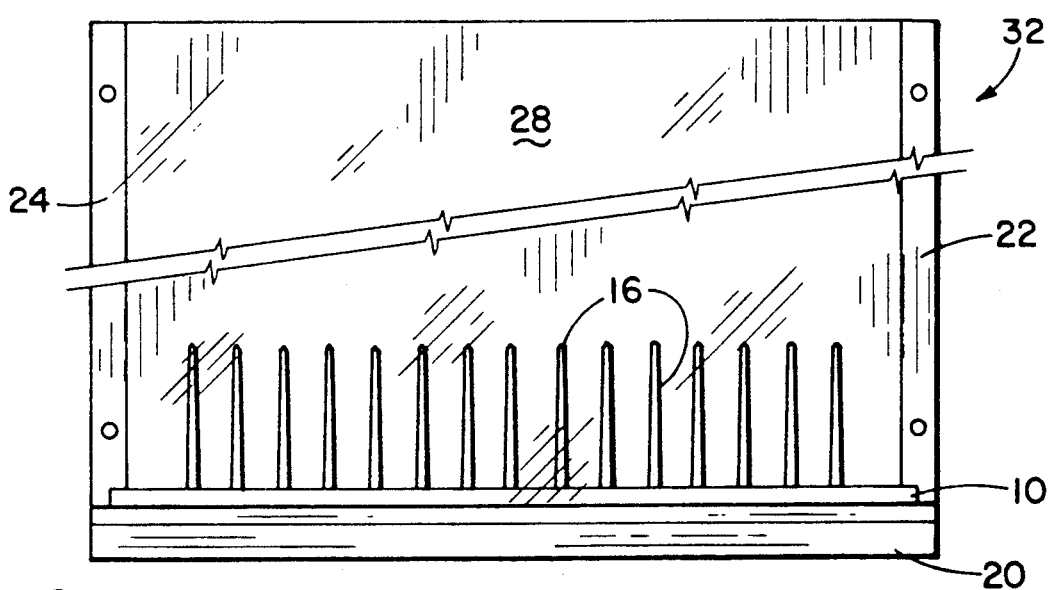
FIG. 2 is an elevational cross-sectional view of the vessel of FIG. 1 with one side panel of the vessel removed to expose the interior arrangement thereof.
Figure 3:
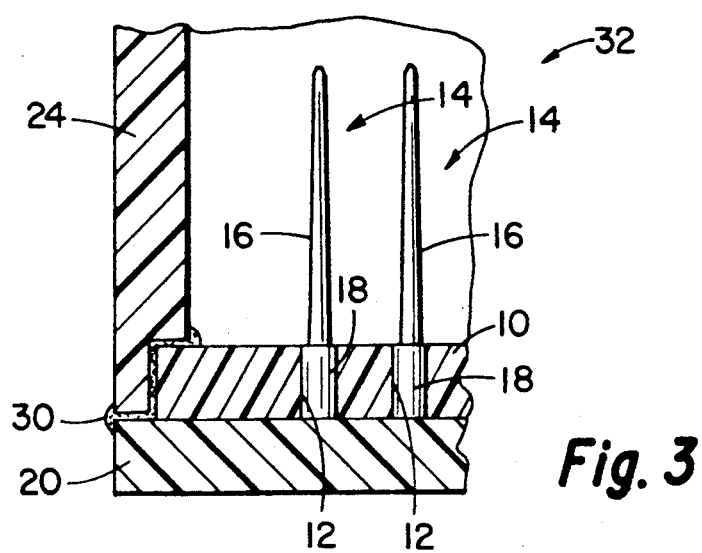
FIG. 3 is a fragmentary enlarged cross-sectional view taken along the line 3—3 of FIG. 1 and showing metal patterns extending upwardly from the bottom member and showing one end panel of the mold vessel.
Figure 4:
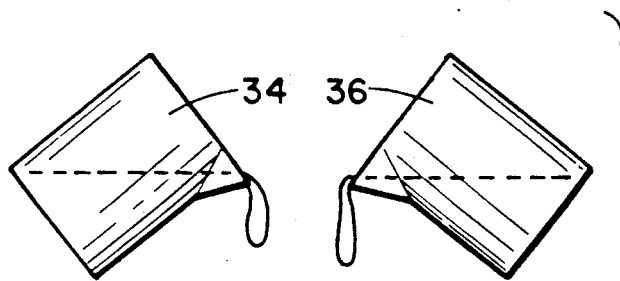
FIG. 4 is a view showing the step of pouring into the formed vessel a liquid plastic material and a catalyst.

After a vessel is formed as illustrated in FIGS. 1-3, liquid plastic and a liquid catalyst, illustrated as being poured from containers 34 and 36 in FIG. 4, are mixed and deposited within the interior of vessel 32. While in FIG. 4, for illustrative purposes only, liquids are illustrated as separately deposited into vessel 32, in actual practice these materials are intimately mixed first and then poured into vessel 32 so that as the liquid enters the vessel, it does not have to be further stirred and therefore is in chemical condition to, with time, solidify.

When uncured liquid plastic and catalyst is poured into a vessel with the intent it be permitted to solidify to take the form of the vessel, air bubbles are an inherent problem. Vessel 32 having air bubbles 38 in the plastic is shown in FIG. 5. The vessel is placed in a vacuum chamber, indicated by the numeral 40 of FIGS. 6 and 7. In chamber 40 a vacuum is applied that causes bubbles entrained within the liquid plastic 42 to be drawn out so that it is substantially bubble free and thereby permitted to closely conform to the interior of vessel 32, that is, to the lower portion of vessel 32 and to a height above vessel base 10 that at least covers the upper ends of the pattern shaft portions 16.

FIG. 7 illustrates vacuum chamber 40 being opened so that vessel 32 can be removed therefrom. After the vessel is removed it remains undisturbed until the liquid plastic 42 solidifies as the reaction with the catalyst is completed. The solidified plastic forms a mold 44, as seen in FIGS. 8, 9 and 10. The mold 44 has horizontal dimensions that are those of the interior of vessel 32. FIG. 8 shows the vessel being disassembled by removing the end panels 22 and 24, and side panels 26 and 28 from bottom 20 and from engagement with base 10. This permits mold 44, that is in the form of a block of solidified plastic, to be removed from the base. Each of the metal shaft portions 16 of the patterns 14 are removed from within the soldified mold 44.

FIG. 9 shows the mold 44 inverted in the manner in which it is used for manufacturing appliances for use in filling endodontically prepared root canals.

As shown in FIG. 9, mold 44 is of rectangular configuration conforming to the interior configuration of vessel 32 and has a plurality of cavities 46 therein, each cavity conforming to the external surface of the shaft portions 16 extending from the cavity bottom.

Mold 44 can be repeatedly used in the manufacture of appliances according to the principles of this invention. It should be pointed out that cavities 46 formed in mold body 44 may be of uniform shape and length or they may be of varying shapes and lengths. Putting it another way, mold 44 may be manufactured by the process described with reference to FIGS. 1-7 to produce a plurality of appliances each having the same shape and diameter with a different mold being used for each different shape and diameter, or a single mold 44 may be manufactured so as to provide for different shapes and lengths.

Mold 44 may be preferably formed of silicone rubber. Successful molds have been made using Dow Corning 3110 silicone rubber mold making material used with Dow Corning catalyst 1. Working time of the material is varied by changing the mixture ratio as prescribed by the manufacturer, with sufficient time being selected to obtain extraction of substantially all of the bubbles in the steps shown in FIGS. 6 and 7 before the material sets up. Undoubtedly, many other types of plastics could be used for forming mold 44 that have not yet been tried.

After mold 44 is available the first step in the manufacturing of appliances is to fill cavities 46 with an endodontic filler material, such as uncured gutta-percha. This can be accomplished by forming tips 48 of uncured gutta-percha. Tips 48 are elongated tapered quantities of gutta-percha, as illustrated in FIG. 10. A tip 48 is inserted into each cavity 46. It is not important that the shape of tips 48 exactly match that of cavities 46—the only important requirement is that the tips be readily inserted into the cavities. FIG. 10 shows a tip 48 ready to be inserted into a cavity 46 and shows two cavities 46 with tips 48 therein.

After each of the cavities 46 is filled with uncured filler material, such as uncured gutta-percha, as illustrated in the step of FIG. 10, a filler carrier, generally indicated by the numeral 50, is inserted into each cavity. A filler carrier, as described specifically with reference to U.S. Pat. No. 4,758,156, has two basic portions, that is, a distal shaft portion 52 and a proximal handle portion 54 that is typically of enlarged external diameter. The shaft portion 52 of a filler carrier 50 is elongated, slender and usually slightly tapered and formed of relatively stiff, but slightly flexible material, such as metal or hard plastic.

A filler carrier shaft portion 52 is inserted into each of the cavities 46. The shaft portions extend within the filler material 48 in each cavity 46 and causes the filler material to conform to the shape of each of the cavities. Tips 48 of gutta-percha inserted into each of the cavities to fill the same are preferably formed so that when a filler carrier shaft portion 52 is inserted into the cavity, the cavity will be completely filled and a portion of the filler material will be forced out of the top of the cavity, the portion being illustrated by the numeral 48A in FIG. 11. This overflow helps to ensure that each cavity is completely filled with the filler material.

After each of the cavities has received a shaft portion 52 of a filler carrier 50 the mold having the filler material and filler carriers therein is placed in an oven, as shown in FIG. 12, the oven being generally indicated by the numeral 56. In the oven the mold 44 and the contents are heated to cause the filler material 48 to cure. The time and temperature necessary for the curing process depends upon the nature of the filler material used. A preferred filler material is gutta-percha. After the proper time at the correct temperature has elapsed, oven 56 with mold 44 therein is allowed to return to room temperature. After that each of the filler carriers 50 is removed from the mold. The filler material 48A adheres to the carrier member shaft portion 52, the cured filler material being indicated in FIG. 13 by the numeral 48B to distinguished from the uncured filler material 48A in FIG. 11, although the configuration of the filler material is substantially identical.

The appliance of FIG. 13 is ready to be used by a dentist or endodontist in filling a prepared root canal. After a root canal is prepared the endodontist selects an appliance having a shaft of nominal diameter to closely fit the root canal to be filled. The endodontist inserts the carrier distal shaft portion 52 to the full depth of the root canal. The carrier shaft portion 52 having the cured filler material 48B thereon thereby fills the root canal quickly and expeditiously.

The technique of making a mold for use in manufacturing endodontic appliances and the process of manufacturing the appliances provides expeditious and efficient methods that substantially reduce the cost of producing appliances and ensures uniformity and a high degree of quality control.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of manufacturing appliances for use in filling endodontically prepared root canals comprising:
    (a) forming a mold having a plurality of spaced apart elongated tapered cavities of selected shape and length, each cavity having a closed bottom and an open top;
    (b) filling each of said cavities with uncured endodontic filler material through said open top;
    (c) then inserting into each said cavity the shaft portion of a filler carrier, the carrier having a handle portion that remains exterior of the mold;
    (d) placing said mold having said uncured filler material and filler carriers therein in an oven;
    (e) heating said mold with said uncured filler material and filler carriers therein to cure said filler material and to cause said filler material to adhere to said filler carrier shaft portions; and
    (f) removing said filler carriers having said filler material cured on the shaft portions thereof, each of which is ready for use as an appliance to fill an endodontically prepared root canal.

2. A method of manufacturing appliances for use in filling endodontically prepared root canals according to claim 1 wherein step (b) comprises filling said cavities with uncured gutta-percha.

3. A method of manufacturing appliances for use in filling endodontically prepared root canals according to claim 2 wherein said step of filling each of said cavities with uncured gutta-percha includes forming uncured gutta-percha into elongated tapered tips and placing a tip into each of said cavities.

4. A method of manufacturing appliances for use in filling endodontically prepared root canals according to claim 1 wherein said step of filling each of said cavities with uncured filler material includes forming uncured filler material into elongated tapered tips and placing a tip into each of said cavities.

5. A method of manufacturing appliances for use in filling endodontically prepared root canals, each appliance having a filler carrier having a distal end portion in the form of a slender shaft and a proximal end handle portion, comprising:

forming a plurality of elongated slender tapered tips of uncured endodontic filler material;

filling a plurality of cavities in a mold with said tips of uncured endodontic filler material, each cavity being elongated and of length and shape of that of the ultimately desired filler encapsulated shaft portion of an appliance;

positioning the distal shaft portion of a filler carrier into each filler filled cavity;

placing the mold having the filler carriers therein in an oven;

heating the mold for a selected time and temperature to cure the filler material and to cause the filler material to adhere to the filler carrier distal shaft portions; and removing the filler carriers having cured filler material adhered to the distal shaft portions, the same being ready for use as appliances to fill endodontically prepared root canals.

* * * * *